US008579968B1

(12) United States Patent
Shannon et al.

(10) Patent No.: US 8,579,968 B1
(45) Date of Patent: Nov. 12, 2013

(54) ADJUSTABLE TRICUSPID RING

(75) Inventors: Frank Shannon, Birmingham, MI (US);
Samuel M. Shaolian, Newport Beach, CA (US); Brian C. Gray, Lake Forest, CA (US); Vincent Yeh, Orinda, CA (US)

(73) Assignee: MiCardia Corporation, Irvine, CA (US)

( * ) Notice: Subject to any disclaimer, the term of this patent is extended or adjusted under 35 U.S.C. 154(b) by 160 days.

(21) Appl. No.: 13/111,179

(22) Filed: May 19, 2011

Related U.S. Application Data (60) Provisional application No. 61/346,296, filed on May 19, 2010.

(51) Int. Cl.
*A61F 2/24* (2006.01)

(52) U.S. Cl.
USPC ........................................ 623/2.37

(58) Field of Classification Search
USPC ................................. 623/2.36–2.37
See application file for complete search history.

(56) References Cited

U.S. PATENT DOCUMENTS

| | | | |
|---|---|---|---|
| 6,749,630 B2 | 6/2004 | McCarthy et al. | |
| 6,908,482 B2 | 6/2005 | McCarthy et al. | |
| 7,877,142 B2 | 1/2011 | Moaddeb et al. | |
| 2006/0184242 A1* | 8/2006 | Lichtenstein | 623/2.37 |
| 2009/0248148 A1 | 10/2009 | Shaolian et al. | |
| 2011/0011443 A1 | 1/2011 | Yata et al. | |
| 2011/0218622 A1 | 9/2011 | Shaolian et al. | |
| 2011/0230961 A1 | 9/2011 | Langer et al. | |
| 2011/0237872 A1 | 9/2011 | Shaolian et al. | |

OTHER PUBLICATIONS

Ton-Nu, Thanh-Thao, et al., "Geometric Determinants of Functional Tricuspid Regurgitation: Insights From 3-Dimensional Echocardiography," Circulation, 2006; 114:143-149; published online Jul. 3, 2006, http://circ.ahajournals.org/by guest on Jan. 3, 2013.
Filsoufi MC, Farzan, et al., "A Three-Dimensional Ring Annuloplasty for the Treatment of Tricuspid Regurgitation," Department of Cardiothoracic Surgery, 2006, pp. 2273-2277, Mount Sinai Hospital, New York, NY.
Dreyfus, Gilles D., et al., "Secondary Tricuspid Regurgitation or Dilatation: Which Should Be the Criteria for Surgical Repair?", Ann Thorac Surg 2005; 79:127-132, http://ats.ctsnetjournals.org/cgi/content/full/79/1/127.
"Taking proven geometry to a new dimension. The Edwards MC3 Tricuspid Annuloplasty System. The Only 3-D ring for tricuspid repair." Edwards Lifesciences LLC, 2006, 4 pps.

* cited by examiner

*Primary Examiner* — William H. Matthews
(74) *Attorney, Agent, or Firm* — Stoel Rives LLP (57) ABSTRACT

Annuloplasty rings reduce or eliminate tricuspid regurgitation and/or tricuspid annulus dilation. An adjustable annuloplasty device includes a ring body having a first free end and a second free end. The ring body includes a shape memory material to provide a shape change to the adjustable annuloplasty device upon activation. The ring body includes a first segment including the first free end and following a curved path corresponding to an anterior leaflet region of a tricuspid annulus, a second segment following a curved path corresponding to a posterior leaflet region of the tricuspid annulus, and a third segment including the second free end and at least partially following a linear path corresponding to a portion of a septal leaflet region of the tricuspid annulus. Activation of the shape memory material changes a dimension of the adjustable annuloplasty device.

6 Claims, 8 Drawing Sheets

Example Activation Movement

Cross-Sectional View

FIG. 5B

IMPLANT

FIG. 6A

ACTIVATION

ADJUSTABLE TRICUSPID RING

RELATED APPLICATION

This application claims the benefit under 35 U.S.C. §119 (e) of U.S. Provisional Application No. 61/346,296, filed May 19, 2010, which is hereby incorporated by reference herein in its entirety.

TECHNICAL FIELD

The present disclosure relates to methods and devices for reinforcing dysfunctional heart valves and other body structures. More specifically, the present invention relates to adjustable annuloplasty rings for tricuspid heart valves.

BACKGROUND OF THE DISCLOSURE

The human heart includes four chambers, which are the left and right atrium and the left and right ventricles. The mitral valve, which allows blood flow in one direction, is positioned between the left ventricle and left atrium. The tricuspid valve is positioned between the right ventricle and the right atrium. The aortic valve is positioned between the left ventricle and the aorta, and the pulmonary valve is positioned between the right ventricle and pulmonary artery. The heart valves function in concert to move blood throughout the circulatory system.

If the valves of the heart do not function properly, due either to disease or congenital defects, the circulation of the blood may be compromised. Diseased heart valves may be stenotic, wherein the valve does not open sufficiently to allow adequate forward flow of blood through the valve, and/or incompetent, wherein the valve does not close completely. Incompetent heart valves cause regurgitation or excessive backward flow of blood through the valve when the valve is closed. For example, certain diseases of the heart valves can result in dilation of the heart and one or more heart valves. When a heart valve annulus dilates, the valve leaflet geometry deforms and causes ineffective closure of the valve leaflets. The ineffective closure of the valve can cause regurgitation of the blood, accumulation of blood in the heart, and other problems.

Diseased or damaged heart valves can be treated by valve replacement surgery, in which damaged leaflets are excised and the annulus is sculpted to receive a replacement valve. Another repair technique that has been shown to be effective in treating incompetence is annuloplasty, in which the effective size of the valve annulus is contracted by attaching a prosthetic annuloplasty repair segment or ring to an interior wall of the heart around the valve annulus. The annuloplasty ring reinforces the functional changes that occur during the cardiac cycle to improve coaptation and valve integrity. Thus, annuloplasty rings help reduce reverse flow or regurgitation while permitting good hemodynamics during forward flow.

Annuloplasty rings may be stiff or flexible, may be open or closed, and may have a variety of shapes including circular, D-shaped, or C-shaped. The configuration of the ring is generally based on the shape of the heart valve being repaired or on the particular application. For example, the tricuspid valve is generally circular and the mitral valve is generally D-shaped. Further, C-shaped rings may be used for tricuspid valve repairs, for example, because it allows a surgeon to position the break in the ring adjacent the atrioventricular (AV) node, thus avoiding the need for suturing at that location.

SUMMARY OF THE DISCLOSURE

In one embodiment, an adjustable annuloplasty device includes a ring body having a first free end and a second free end, the ring body comprising a shape memory material to provide a shape change to the adjustable annuloplasty device upon activation. The body includes a first segment including the first free end and following a curved path corresponding to an anterior leaflet region of a tricuspid annulus, a second segment following a curved path corresponding to a posterior leaflet region of the tricuspid annulus, and a third segment including the second free end and at least partially following a linear path corresponding to a portion of a septal leaflet region of the tricuspid annulus. The activation of the shape memory material results in a reduction of an anterior/septal height of the adjustable annuloplasty device.

In certain embodiments, the adjustable annuloplasty device further includes a subcutaneous activation cable comprising a distal end attached to the adjustable annuloplasty ring at a location corresponding to the second segment, wherein the subcutaneous activation cable provides energy to activate the shape memory material.

In certain embodiments, the adjustable annuloplasty device further includes a subcutaneous activation cable comprising a distal end attached to the adjustable annuloplasty ring at a junction between second segment and the third segment, wherein the subcutaneous activation cable provides energy to activate the shape memory material.

In certain embodiments, the activation of the shape memory material does not substantially change the width of the adjustable annuloplasty device.

In certain embodiments, the activation of the shape memory material does not substantially change an overall length of the adjustable annuloplasty device.

In certain embodiments, the activation of the shape memory material reduces a distance between the first free end and an axis corresponding to the linear path of the third segment. In certain such embodiments, a gap between the first end and the second end remains sufficient as a result of the activation to avoid interference of the adjustable annuloplasty device with the atrioventricular node or coronary sinus.

BRIEF DESCRIPTION OF THE DRAWINGS

The present embodiments will become more fully apparent from the following description and appended claims, taken in conjunction with the accompanying drawings. Understanding that the accompanying drawings depict only typical embodiments, and are, therefore, not to be considered to be limiting of the disclosure's scope, the embodiments will be described and explained with specificity and detail in reference to the accompanying drawings.

DETAILED DESCRIPTION OF PREFERRED EMBODIMENTS

The embodiments disclosed herein are directed to reducing or eliminating tricuspid regurgitation and/or tricuspid annulus dilation. As discussed above, annuloplasty is used to restore an optimal shape, provide support, and prevent further annular dilation. Tricuspid valve dilation is related to tricuspid valve regurgitation. Isolated tricuspid valve disease may be relatively rare. It usually accompanies other valve pathology, particularly mitral valve disease.

Figure 1A:
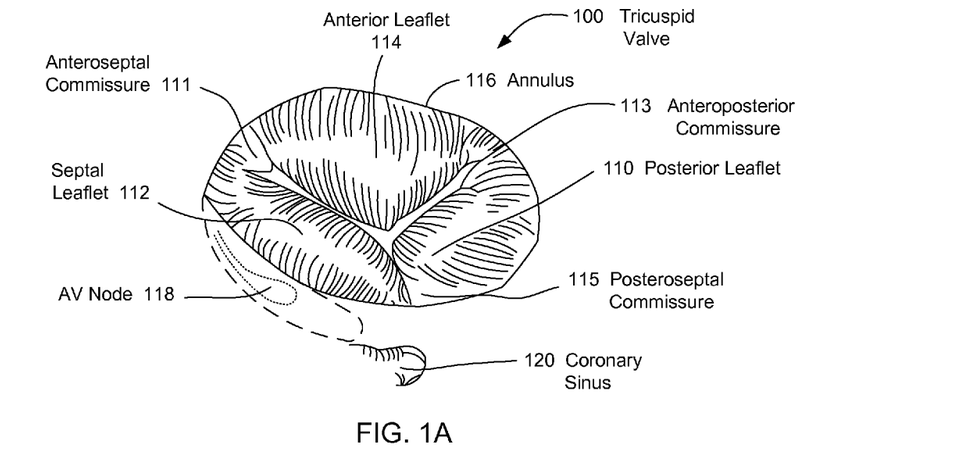
FIGS. 1A and 1B are plan views of the tricuspid valve and some surrounding anatomy.
Figure 1B:
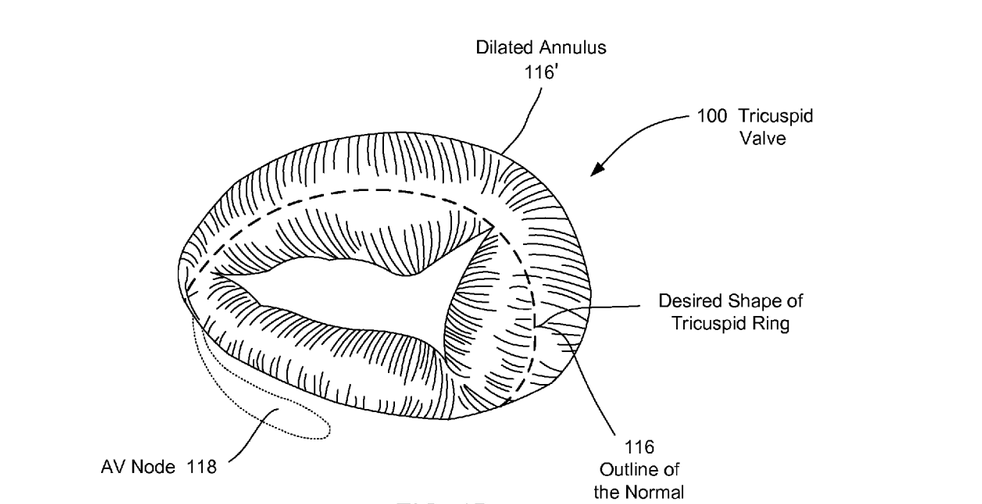

FIGS. 1A and 1B are plan views of a tricuspid valve 100 and some surrounding anatomy. The tricuspid valve 100 is the right atrial valve counterpart to the mitral valve (not shown). The tricuspid valve 100 is made up of three leaflets: a posterior leaflet 110, a septal leaflet 112, and an anterior leaflet 114. The leaflets 110, 112, 114 are separated by respective commissures referred to as the anteroseptal commissure 111, the anteroposterior commissure 113, and the posteroseptal commissure 115. Unlike the mitral valve, the tricuspid valve 100 functions in a low pressure system. The tricuspid annulus 116 is not in a single flat plane. Further, the septal portion of the tricuspid annulus 116 is an integral part of the fibrous skeleton of the heart. The atrioventricular (AV) node 118 (which is part of the heart's electrical conduction system) is located close to but above the anterior insertion of the septal leaflet 112. FIG. 1A also shows the general location of the coronary sinus 120 with respect to the tricuspid valve 100. Of course, when implanting an annuloplasty ring, surgeons should avoid placing sutures too close to or within the AV node 118. The implanted annuloplasty ring also should not interfere with the coronary sinus 120.

FIG. 1B illustrates the tricuspid valve 100 with a dilated annulus 116'. The dilated annulus 116' is shown with respect to an outline of the normal sized annulus 116 (illustrated with a dashed line). The dashed line may also represent a desired shape and size of an annuloplasty ring (or "tricuspid ring" discussed in detail below) that provides sufficient support for the tricuspid valve.

As discussed below, certain embodiments of the tricuspid ring reduce the anterior/septal leaflet height. The tricuspid ring may be discontinuous near the anteroseptal commissure 111 to prevent interaction with the AV node 118. Further, the tricuspid ring may include two or three (or more) sections or zones that correspond to the annular circumference of the tricuspid leaflets 110, 112, 114. In one embodiment, for example, the following ratio is followed: the circumference of the anterior leaflet portion of the tricuspid ring is a minimum of three times longer than the posterior leaflet portion of ring; and the length of the septal portion of the tricuspid ring is no more than 80% of the anatomical length of the tricuspid annulus 116. A labeled size of the tricuspid ring may be based on the annular diameter from the anteroseptal commissure 111 to the anteroposterior commissure 113. The height and width of the tricuspid ring may have a ratio, for example, of about 0.68. An anterior/septal leaflet height reduction of about 2 mm to about 4 mm may be used in certain embodiments to eliminate or reduce tricuspid regurgitation.

Figure 2:
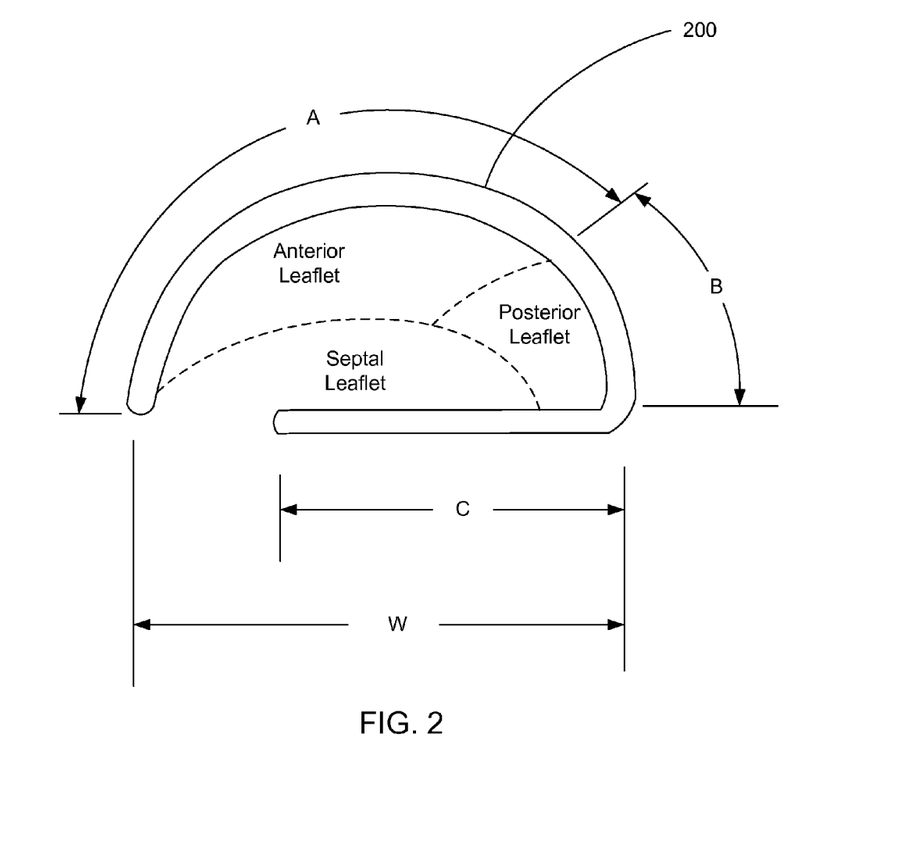
FIG. 2 is a plan view of a tricuspid ring having three sections according to one embodiment.

FIG. 2 is a plan view of a tricuspid ring 200 having three sections according to one embodiment. In FIG. 2, the sections are labeled "A," "B," and "C." For illustrative purposes, the sections A, B, and C are labeled with respect to anterior, posterior, and septal leaflets (shown with dashed lines) of the tricuspid valve 100 (see FIGS. 1A and 1B). Sections A and B are curved. With respect to FIGS. 1A, 1B, and 2, section A may be configured for implantation around the anterior leaflet 114 along the annulus 116 of the tricuspid valve 100. Thus, the length of section A may be approximately the length of the anterior leaflet annulus. The open end of section A may extend past the anteroseptal commissure 111 and provides an opening in the tricuspid ring 200 that avoids the AV node 118. Section B may be configured for implantation around the posterior leaflet 110 along the annulus 116 of the tricuspid valve 100. Thus, the length of section B may be approximately the length of the posterior leaflet annulus. In one embodiment, the ratio A/B is about 3/1 (or 3:1). This 3:1 ratio approximately corresponds to the ratio of the circumference of the anterior leaflet 114 to the circumference of the posterior leaflet 110. In the illustrated embodiment, section C is substantially straight or linear and may be configured for implantation along a portion of the septal leaflet 112. The length of section C may be selected so as to avoid the AV node 118. In one embodiment, for example, the length of section C is about 80% of the overall width W of the tricuspid annulus 116.

In an example embodiment, dimensions corresponding to various sizes of the tricuspid ring 200 shown in FIG. 2 are described in Table 1.

TABLE 1

| Example Tricuspid Dimensions | | | | | |
|---|---|---|---|---|---|
| Ring Size | Anterior Leaflet Width (mm) | Ratio (Height/Width) | Valve Height (mm) | Height Reduction (mm) | Activated Shape Height (mm) |
| 27 | 27.00 | 0.62 | 16.74 | 2.00 | 14.74 |
| 29 | 29.00 | 0.62 | 17.98 | 3.00 | 14.98 |
| 31 | 31.00 | 0.62 | 19.22 | 3.00 | 16.22 |
| 33 | 33.00 | 0.62 | 20.46 | 3.00 | 17.46 |
| 35 | 35.00 | 0.62 | 21.70 | 4.00 | 17.70 |

The size of the tricuspid ring 200 can be "activated" or adjusted postoperatively to compensate for changes in the size of the heart. Thus, Table 1 shows an activated shape height. As used herein, "postoperatively" refers to a time after implanting the adjustable tricuspid ring 200 and closing the body opening through which the adjustable tricuspid ring 200 was introduced into the patient's body. For example, the tricuspid ring 200 may be implanted in a child whose heart grows as the child gets older. Thus, the size of the tricuspid ring 200 may need to be increased. As another example, the size of an enlarged heart may start to return to its normal size after an tricuspid ring 200 is implanted. Thus, the size of the tricuspid ring 200 may need to be decreased postoperatively to continue to reinforce the heart valve annulus 116. In other embodiments, the size of the tricuspid ring 200 may be adjusted soon after being implanted. For example, the size of the annuloplasty ring 200 may be adjusted before closing the patient's chest to achieve a desired result, such as a reduced amount of regurgitation.

The tricuspid ring 200 includes a shape memory material that is responsive to changes in temperature and/or exposure to a magnetic field. Shape memory is the ability of a material to regain its shape after deformation. Shape memory materials include polymers, metals, metal alloys and ferromagnetic alloys. In one embodiment, the tricuspid ring 200 includes shape memory nitinol (NiTi). The tricuspid ring 200 may be adjusted in vivo by applying an energy source (not shown) to activate the shape memory material and cause it to change to a memorized shape. The energy source may include, for example, radio frequency (RF) energy, x-ray energy, microwave energy, ultrasonic energy such as focused ultrasound, high intensity focused ultrasound (HIFU) energy, light energy, electric field energy, magnetic field energy, combinations of the foregoing, or the like. In some embodiments, fine conductive wires (not shown) such as platinum coated copper, titanium, tantalum, stainless steel, gold, or the like, are wrapped around the shape memory material to allow focused and rapid heating of the shape memory material while reducing undesired heating of surrounding tissues.

In certain embodiments, the energy source is applied surgically either during implantation or at a later time. For example, the shape memory material can be heated during implantation of the tricuspid ring 200 by touching the tricuspid ring 200 with a warm object. As another example, the energy source can be surgically applied after the tricuspid ring has been implanted by percutaneously inserting a catheter into the patient's body and applying the energy through the catheter. For example, RF energy, light energy or thermal energy (e.g., from a heating element using resistance heating) can be transferred to the shape memory material through a catheter positioned on or near the shape memory material. Alternatively, thermal energy can be provided to the shape memory material by injecting a heated fluid through a catheter or circulating the heated fluid in a balloon through the catheter placed in close proximity to the shape memory material. As another example, the shape memory material can be coated with a photodynamic absorbing material that is activated to heat the shape memory material when illuminated by light from a laser diode or directed to the coating through fiber optic elements in a catheter. In certain such embodiments, the photodynamic absorbing material includes one or more drugs that are released when illuminated by the laser light.

In certain embodiments, a removable or non-removable subcutaneous electrode or coil couples energy from a dedicated activation unit. In certain such embodiments, the removable subcutaneous electrode provides telemetry and power transmission between the system and the tricuspid ring. The subcutaneous electrode allows more efficient coupling of energy to the implant with minimum or reduced power loss. In certain embodiments, the subcutaneous energy is delivered via inductive coupling.

In other embodiments, the energy source is applied in a non-invasive manner from outside the patient's body. In certain such embodiments, the external energy source is focused to provide directional heating to the shape memory material so as to reduce or minimize damage to the surrounding tissue. For example, in certain embodiments, a handheld or portable device comprising an electrically conductive coil generates an electromagnetic field that non-invasively penetrates the patient's body and induces a current in the tricuspid ring. The current heats the tricuspid ring and causes the shape memory material to transform to a memorized shape. In certain such embodiments, the tricuspid ring also comprises an electrically conductive coil wrapped around or embedded in the memory shape material. The externally generated electromagnetic field induces a current in the tricuspid ring's coil, causing it to heat and transfer thermal energy to the shape memory material.

The tricuspid ring may also include a suturable material (not shown). The suturable material is disposed about the shape memory material to facilitate surgical implantation of the tricuspid ring in a body structure, such as about a heart valve annulus. In certain embodiments, the suturable material comprises a suitable biocompatible material such as Dacron®, woven velour, polyurethane, polytetrafluoroethylene (PTFE), heparin-coated fabric, or the like. In other embodiments, the suturable material comprises a biological material such as bovine or equine pericardium, homograft, patient graft, or cell-seeded tissue. The suturable material may be disposed about the entire circumference of the tricuspid ring, or selected portions thereof.

Figure 3:
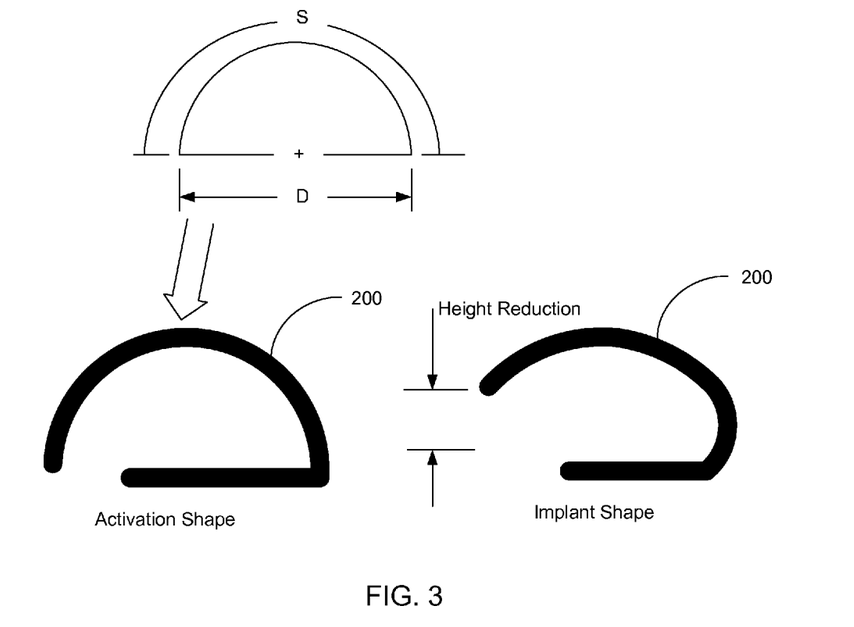
FIG. 3 schematically illustrates an implant shape and an activation shape of a tricuspid ring, such as the tricuspid ring shown in FIG. 2, according to one embodiment.

FIG. 3 schematically illustrates an implant shape and an activation shape of a tricuspid ring 200, such as the tricuspid ring shown in FIG. 2, according to one embodiment. For reference, FIG. 3 also schematically illustrates a circumference S and a diameter D corresponding to the tricuspid ring 200.

FIG. 3 also illustrates a height reduction in the open end of the tricuspid ring 200 between the implant shape and the activation shape. Note that in certain embodiments the difference between the implant shape and the activation shape occurs without changing the length of the shape memory material (e.g., shape memory wire).

In certain embodiments, the tricuspid ring 200 comprises a heater coil (not shown) wrapped around a shape memory wire core (not shown). Example heating coils and shape memory wire cores are disclosed in International Application No. PCT/US2010/042644, having international filing date Jul. 20, 2010, and having International Publication No. WO 2011/011443, the entirety of which is hereby incorporated by reference herein for all purposes. In this embodiment, the heater coil comprises nickel chromium (NiCr) and the shape memory wire core comprises nitinol (NiTi).

Figure 4:
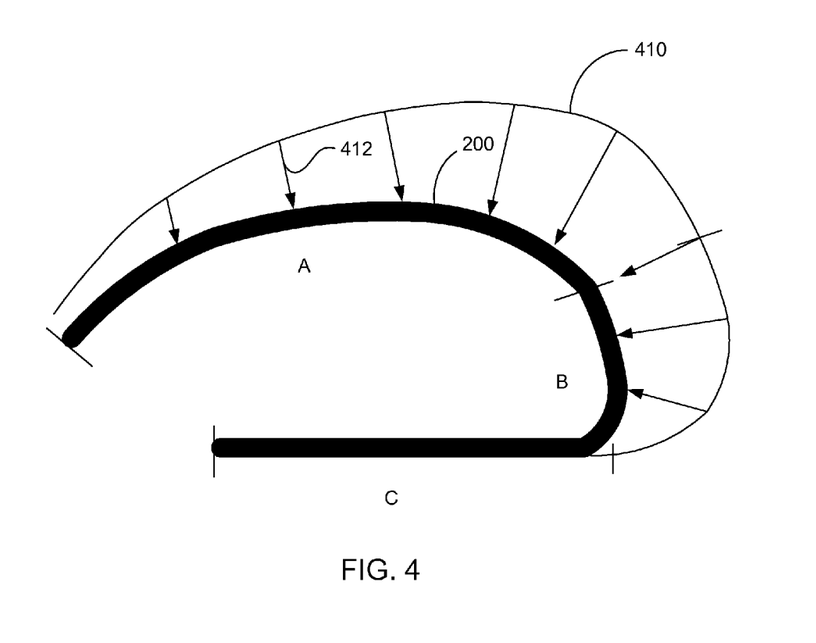
FIG. 4 schematically illustrates an activated shape of a tricuspid ring according to one embodiment.

FIG. 4 schematically illustrates an activated shape of a tricuspid ring 200 according to one embodiment. For illustrative purposes in FIG. 4, the tricuspid ring 200 is represented in the activated state and a line 410 represents the tricuspid ring 200 before activation (e.g., as initially implanted). Further, as discussed with respect to FIG. 2, sections A, B, and C are illustrated with respect to the activated shape of the tricuspid ring 200. Arrows 412 (eight shown) represent vectors showing the direction of movement during activation from the larger ring size to the smaller ring size. In the activated state, the ratio of section A to section B in this example is about A/B=3.5/1. Thus, there is a greater reduction in the circumference of section A than in the circumference of section B. In one embodiment, the length of section C remains approximately the same before and after activation. In another embodiment, the length of section C decreases during activation by about 10% to 15%. A net result of activation is a change in the tricuspid ring to more of an ellipse, rather than an oval.

In certain embodiments described herein, the tricuspid ring 200 is planar. In other words, the tricuspid ring 200 has a nominal cross-sectional centerline that assumes a two-dimensional shape that lies in a single plane. In such embodiments, the shape change also only occurs within the same plane. In other embodiments, three-dimensional tricuspid rings may also be used, and/or activation may cause the tricuspid ring 200 to change from a two-dimensional ring to a three dimensional ring.

Figure 5A:
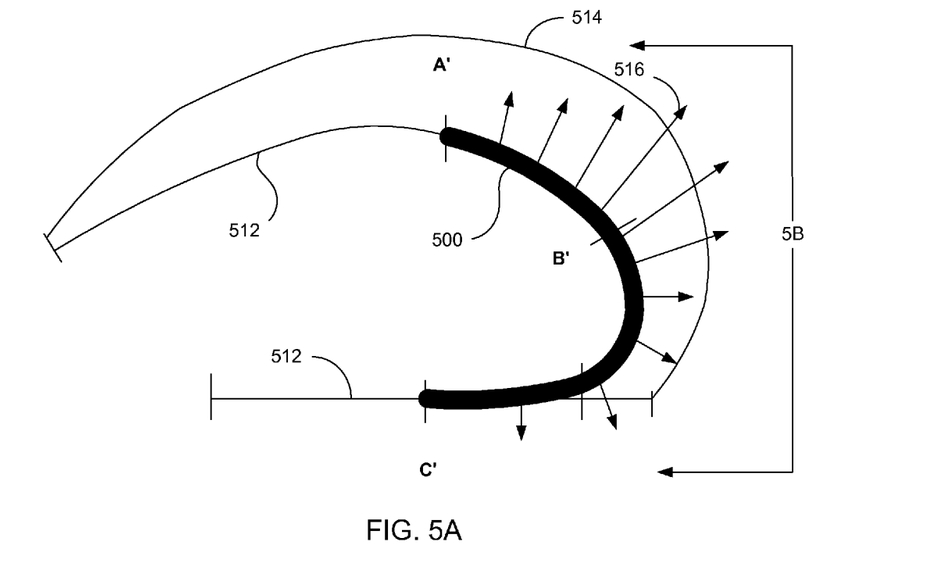
FIGS. 5A and 5B schematically illustrate a tricuspid ring configured to extend out of a plane as a result of shape activation according to one embodiment.
Figure 5B:
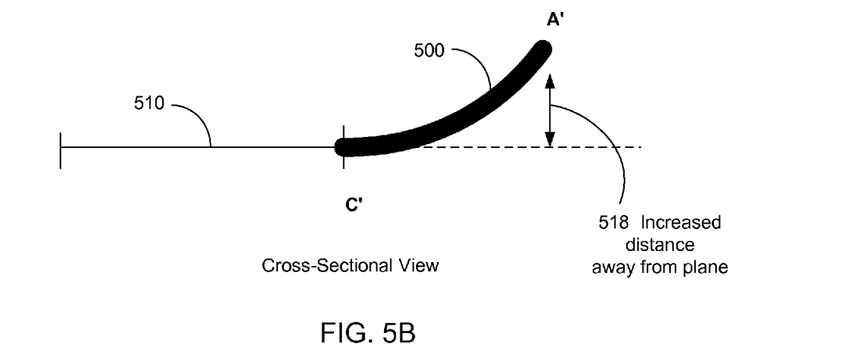

For example, FIGS. 5A and 5B schematically illustrate a tricuspid ring 500 configured to extend out of a plane 510 (shown in FIG. 5B) as a result of shape activation according to one embodiment. FIG. 5A shows the tricuspid ring 500 before activation and FIG. 5B shows the tricuspid ring 500 after activation. For illustrative purposes, a relatively thin line 512 passing through the tricuspid ring 500 represents the activated shape of the tricuspid ring 200 shown in FIG. 4, and a relatively thin line 514 represents the unactivated shape corresponding to line 410 shown in FIG. 4. The arrows 516 (ten shown in FIG. 5A) represent vectors indicating the direction of movement during activation from a smaller ring size to a larger ring size. As shown in FIG. 5A, the overall length of the tricuspid ring 500 is much smaller, both before and after activation, in this embodiment than that of the tricuspid ring 200 shown in FIG. 4.

Activation of the tricuspid ring 500 shown in FIG. 5A results in changing the circumferential lengths of sections A' and B'. As shown by arrow 518 in FIG. 5B, activation also results in an upsloping curve out of the plane 510 from C' to A'. In some embodiments, a maximum height of the upsloping curve out of the plane 510 occurs at approximately the transition point between sections B' and A'. The septal arm (C') of the tricuspid ring 500 may contribute to the sloping in the third dimension, along with sections A' and B'. FIG. 5B shows the increased distance away from the plane 510 (as represented by arrow 518). In some embodiments, this increased distance may be about 10%.

Figure 6A:
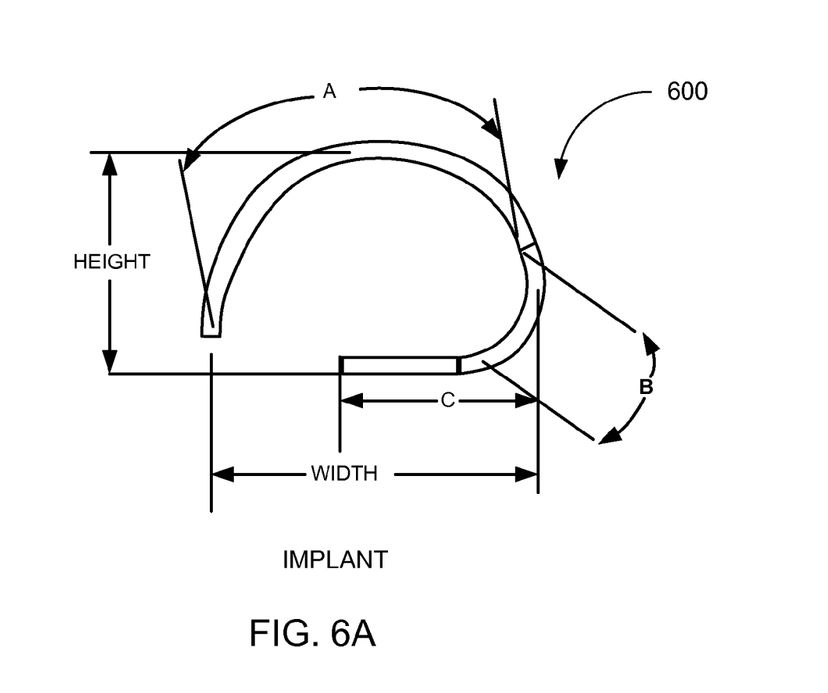
FIGS. 6A, 6B, and 6C are plan views of a tricuspid ring according to one embodiment.
Figure 6B:
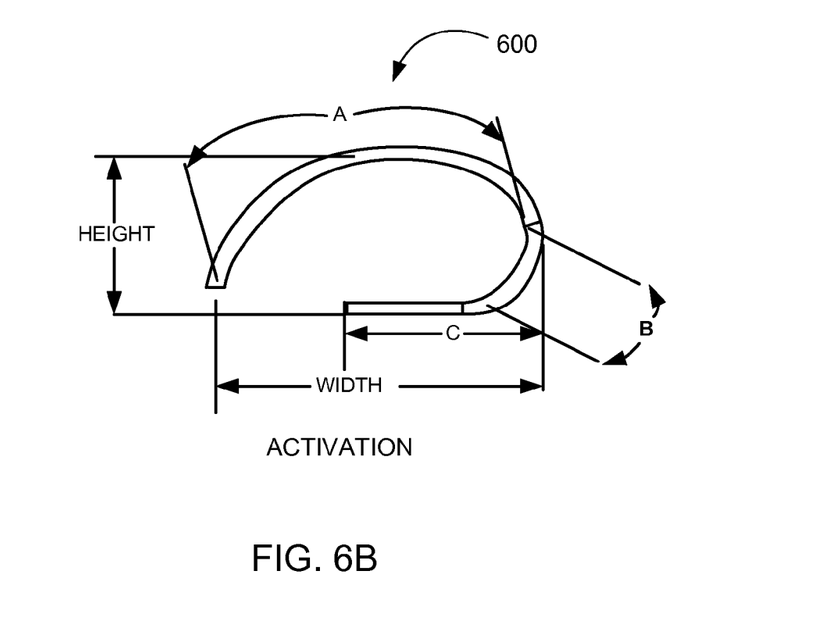
Figure 6C:
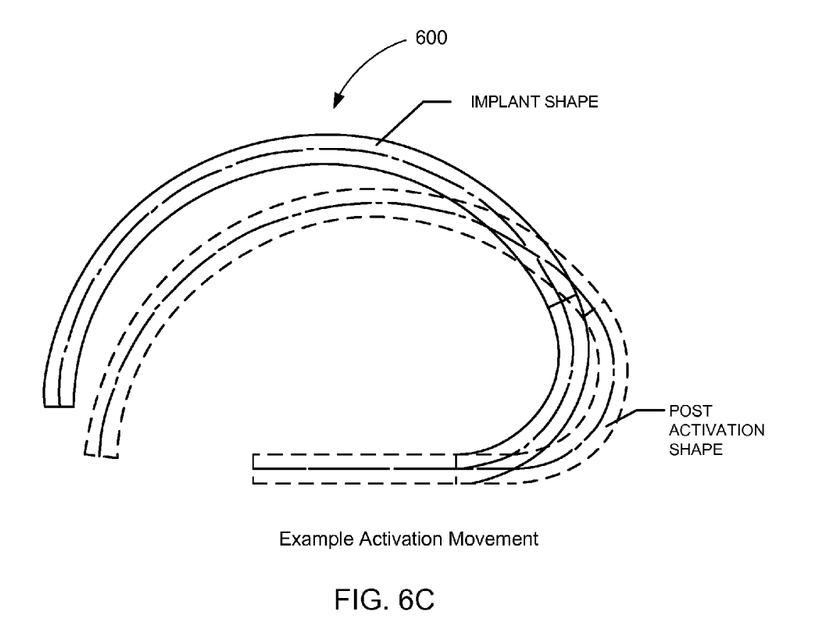

FIGS. 6A, 6B, and 6C are plan views of a tricuspid ring 600 according to one embodiment. FIG. 6A illustrates a shape of the tricuspid ring 600 as initially implanted around the tricuspid annulus 116 (see FIG. 1A). FIG. 6B illustrates a shape of the tricuspid ring 600 after activation. For comparison purposes, FIG. 6C illustrates overlapping views of the implant shape and the post activation shape of the tricuspid ring 600, wherein the implant shape is shown with a solid line and the post activation shape is shown with a dashed line. Activation causes a reduction in the anterior/septal leaflet height of the tricuspid valve 100 (e.g., in FIG. 6C, the reduced anterior/septal height corresponds to a reduction in the vertical direction). See Table 1 for example dimensions for various sizes of the tricuspid ring 600 shown in FIGS. 6A, 6B, and 6C.

Figure 7A:
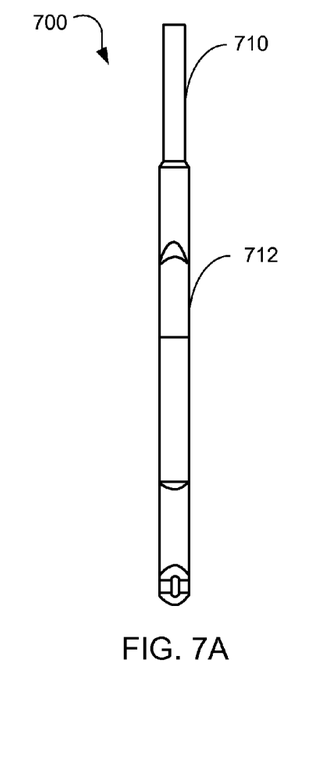
FIGS. 7A and 7B schematically illustrate a side view and a plan view of a tricuspid ring assembly comprising a subcutaneous activation cable attached to a tricuspid ring according to one embodiment.
Figure 7B:
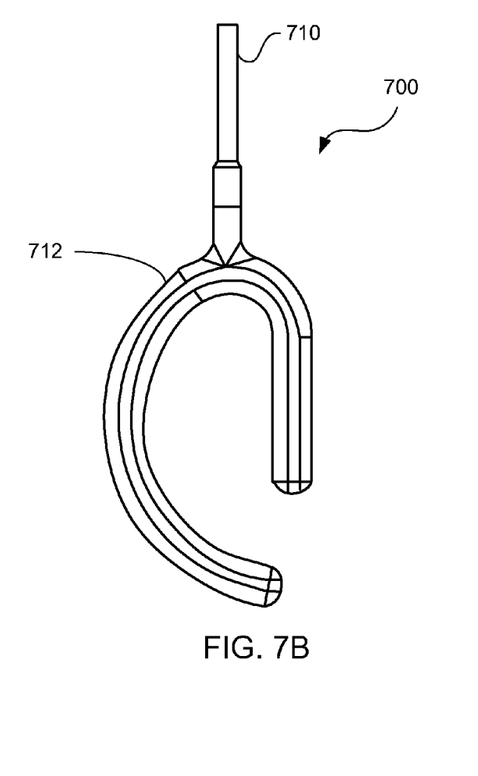

FIGS. 7A and 7B schematically illustrate a side view (FIG. 7A) and a plan view (FIG. 7B) of a tricuspid ring assembly 700 comprising a subcutaneous activation cable 710 attached to a tricuspid ring 712 according to one embodiment. As discussed in International Publication No. WO 2011/011443, which is incorporated by reference herein, the subcutaneous activation cable 710 may be used to provide RF energy to change the shape of the tricuspid ring 712.

As shown in FIGS. 7A and 7B, the subcutaneous activation cable 710 arises from or is attached to the tricuspid ring 712 at a junction of the straight portion (e.g., corresponding to the septal leaflet region) of the tricuspid ring 712 with the beginning of the curved portion of the tricuspid ring 712 (e.g., the posterior leaflet region). When implanted, the subcutaneous activation cable 710 then exits the right atrium in a "natural" position, i.e., lateral to the coronary sinus, above the AV groove out into the pericardial free space. For exit of the subcutaneous activation cable from the heart, it may be useful to pursue as straight a course as possible without injuring or obstructing the coronary sinus. The subcutaneous activation cable 710 may be passed through the atrial wall, so as not to injure any AV or coronary sinus structures.

The tricuspid ring 712 shown in FIGS. 7A and 7B is planar. In other embodiments, however, the tricuspid ring 712 may be non-planar in that it has a cross-sectional centerline that assumes a three-dimensional shape such that does not lie in a single plane. This may allow the tricuspid 712 ring to better conform to the shape of the tricuspid annulus. The tricuspid ring 712 may have a three-dimensional shape before and/or after activation.

It will be understood by those having skill in the art that many changes may be made to the details of the above-described embodiments without departing from the underlying principles of the invention.

The invention claimed is:

1. An adjustable annuloplasty device, comprising:
a ring body having a first free end and a second free end, the ring body comprising a shape memory material to provide a shape change to the adjustable annuloplasty device in response to activation energy, the ring body including:
a first segment including the first free end and following a curved path corresponding to an anterior leaflet region of a tricuspid annulus;
a second segment following a curved path corresponding to a posterior leaflet region of the tricuspid annulus; and
a third segment including the second free end and at least partially following a linear path corresponding to a portion of a septal leaflet region of the tricuspid annulus,
wherein application of the activation energy to the shape memory material reduces a length of the first segment, reduces a length of the second segment, and changes a dimension of the adjustable annuloplasty device,
wherein the application of the activation energy reduces the length of the first segment more than it reduces the length of the second segment, and
wherein the application of the activation energy reduces a distance between the first free end and an axis corresponding to the linear path of the third segment.

2. The adjustable annuloplasty device of claim 1, wherein the dimension comprises an anterior/septal height of the ring body, and wherein the application of the activation energy to the shape memory material results in a reduction of the anterior/septal height of the ring body.

3. The adjustable annuloplasty device of claim 2, wherein the anterior/septal height reduction is in a range between 2 mm and 4 mm to eliminate or reduce tricuspid regurgitation.

4. The adjustable annuloplasty device of claim 2, wherein the application of the activation energy to the shape memory material does not substantially change a width of the ring body.

5. The adjustable annuloplasty device of claim 2, wherein the application of the activation energy to the shape memory material does not substantially change an overall length of the ring body.

6. The adjustable annuloplasty device of claim 1, wherein a gap between the first free end and the second free end remains sufficient as a result of the application of the activation energy to avoid interference of the adjustable annuloplasty device with an atrioventricular node or coronary sinus.

* * * * *